(12) United States Patent
Felice et al.

(10) Patent No.: US 7,201,037 B2
(45) Date of Patent: *Apr. 10, 2007

(54) MAIL TUB WITH AIR PORTS

(75) Inventors: Robert J. Felice, Endicott, NY (US); Patrick J. Fitzgibbons, Newark Valley, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/314,631

(22) Filed: Dec. 9, 2002

(65) Prior Publication Data
US 2003/0136179 A1 Jul. 24, 2003

Related U.S. Application Data

(60) Provisional application No. 60/340,118, filed on Dec. 10, 2001.

(51) Int. Cl.
*G01N 19/10* (2006.01)
*B65D 85/00* (2006.01)

(52) U.S. Cl. ............ 73/31.03; 73/28.01; 73/864.33; 206/425

(58) Field of Classification Search ............ 73/31.03, 73/28.01, 864.33; 206/425
See application file for complete search history.

(56) References Cited

U.S. PATENT DOCUMENTS

| 3,300,128 | A | * | 1/1967 | Edward et al. ............ 232/17 |
| 3,756,167 | A | * | 9/1973 | Wilson .................... 108/57.14 |
| 3,915,339 | A | | 10/1975 | Matson |
| 4,580,440 | A | | 4/1986 | Reid et al. |
| 4,593,816 | A | | 6/1986 | Langenbeck |
| 4,863,096 | A | * | 9/1989 | Thomas ..................... 232/17 |
| 5,700,426 | A | | 12/1997 | Schmitthaeusler et al. |
| 5,942,699 | A | * | 8/1999 | Ornath et al. ............ 73/863.21 |
| 6,179,152 | B1 | * | 1/2001 | Sarnowski .................. 220/549 |
| 6,318,586 | B1 | * | 11/2001 | Frankenberg ............... 220/826 |
| 6,524,846 | B1 | * | 2/2003 | Robinson, Jr. ........... 435/287.4 |
| 6,742,703 | B2 | | 6/2004 | Esakov et al. |
| 2001/0029793 | A1 | | 10/2001 | Moler et al. .............. 73/863.22 |
| 2003/0086821 | A1 | * | 5/2003 | Matthews .................... 422/29 |
| 2003/0129111 | A1 | * | 7/2003 | Miller et al. ................ 422/292 |
| 2003/0136203 | A1 | * | 7/2003 | Yoon ........................ 73/864.33 |
| 2003/0222132 | A1 | | 12/2003 | Esakov et al. |

FOREIGN PATENT DOCUMENTS

EP 0169057 A2 1/1986

OTHER PUBLICATIONS

Merriam-Webster's Collegiate Dictionary, 10th edition, pp. 32, 191, and 894.*

(Continued)

*Primary Examiner*—Michael Cygan
(74) *Attorney, Agent, or Firm*—Burns & Levinson LLP; Jacob N. Erlich; Harvey Kaye

(57) ABSTRACT

A mail tub in the form of a substantially rigid container and a removable lid which seals the container. The container includes an air inlet port and an air outlet port for sampling air in the mail tub for possible biological contamination, such as anthrax. The container includes structure along the bottom and walls to prevent mail from contacting the walls and bottom. Such structure, in one embodiment, may include raised standoffs along the bottom of the container and channels along the walls to facilitate airflow efficiency through the mail tub when the lid is attached and an air pressure source is applied to the one of the ports. Air samples of the sealed container air are collected for contamination analysis.

19 Claims, 3 Drawing Sheets

OTHER PUBLICATIONS

U.S. Appl. No. 60/330,808.*
U.S. Appl. No. 60/337,564.*
U.S. Appl. No. 60/340,118, filed Dec. 10, 2001, Robert J. Felice et al.
Copending U.S. Appl. No. 10/282,977, filed Oct. 29, 2002, John T. Bekert et al.
Copending U.S. Appl. No. 10/341,033, filed Jan. 13, 2003, William Harris.
Copending U.S. Appl. No. 10/201,169, filed Jul. 22, 2002, John T. Swider.
Copending U.S. Appl. No. 10/328,230, filed Dec. 23, 2002, John T. Swider.
Copending U.S. Appl. No. 10/328,264, filed Dec. 23, 2002, James M Abulencia et al.
Copending U.S. Appl. No. 10/277,069, filed Oct. 21, 2002, Clifford A. Megerle.
Copending U.S. Appl. No. 10/289,810, filed Nov. 7, 2002, Clifford A. Megerle.
International Search Report, Oct. 21, 2003, PCT/US02/34375 (12078-197PCT).
WO 03/081214A2, Published PCT International Application, Publication Date Oct. 2, 2003, PCT/US02/34375 (12078-197PCT).
U.S. Postal Service Emergency Preparedness Plan for Protecting Postal Employees and Postal Customers from Exposure to Biohazardous Material and for Ensuring Mail Security Against Bioterror Attacks; Mar. 6, 2002; published by USPS.

* cited by examiner

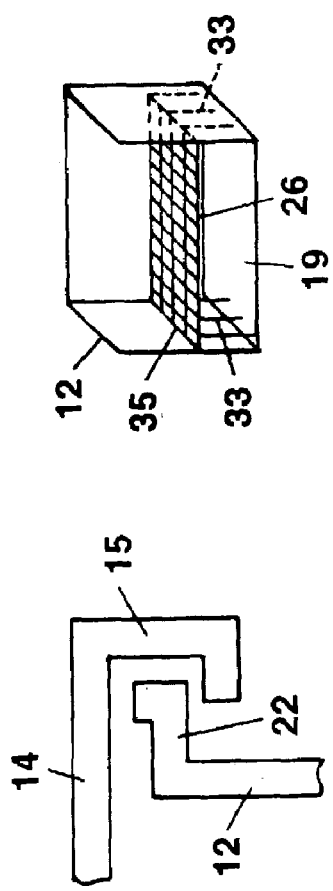
FIG. 3B
FIG. 3A
FIG. 2
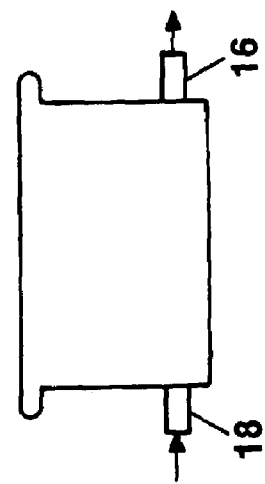
FIG. 4C
FIG. 4B
FIG. 4A

MAIL TUB WITH AIR PORTS

CROSS-REFERENCE TO RELATED APPLICATIONS

This application claims priority of Provisional Application Ser. No. 60/340,118, entitled "MAIL TUB WITH VACUUM PORTS," filed Dec. 10, 2001.

BACKGROUND OF THE INVENTION

This invention relates generally to the containment of hazardous material in an enclosure, and, more particularly to the containment within a mail tub of a biological agent or the like disposed on or in a mail piece.

The recent incidents of anthrax laced letters being transported through the United States Postal Service (USPS) facilities to unsuspecting recipients has alarmed the nation and the world. Currently, the tainted letters are discovered after the recipient accepts delivery or by alert postal employees noticing white powder that could be anthrax on mail parcels, sorting and distribution equipment, or themselves. There appears to be few current security devices or procedures that are available to intercept such letters at the earliest source of introduction into the USPS system, for example at the mailbox or post office drop box. Also, there appears to be no known devices or procedures that safe guard against biological agents in forms other than a white powdery substance, such as anthrax.

Currently when there is suspicious mail, it is all bulk irradiated as was done during the recent anthrax problem thereby delaying some mail for months and damaging or destroying some of the mail due to problems caused by the irradiation. For example some of this irradiated mail became brittle and pieces broke off.

Almost all mail articles at one time or another are collected and transported to postal facilities by way of mail tubs. Therefore, mail tubs can be the first point of containment if a hazardous material is detected prior to the exposure of its air and contents at a postal facility.

Some mail tubs have lids or covers, but they are not airtight vessels. Mail articles that contain hazardous material within or on the outer surface contaminated not only the other mail articles within the mail collection tub, but also the mail collection tub air. The agitation of the mail collection tub in transport or by routine handling by the postal employees can cause the hazardous material to form a plume or aerosol. There is also a threat of contaminating postal employees by inhaling the contaminated air as well as by direct contact to skin tissue.

U.S. Pat. No. 3,915,339 discloses use of pressurized air into a container to loosen and cause free flow of material therein move.

U.S. Pat. No. 4,580,440 discloses a method of detecting a contraband substance in freight cargo in which the container is agitated to disturb particulates therein and samples are taken of the air containing such particulates. The collected particulates are heated to drive off vapors indicative of the contraband substance and the vapors are analyzed in a mass analyzer.

U.S. Pat. No. 4,593,816 discloses a container for storing and transporting letter mail and other flat articles having walls with rib members including on the bottom and the cover to provide structural integrity for the container. The ribs are vertically positioned along the height of the walls and continue across the bottom to form similar verticals ribs on the opposite wall. Adjacent ribs can be made so that dividers can be supported between them. The containers are arranged to be nested when the covers are off and stacked when the covers are on.

U.S. Pat. No. 5,700,426 discloses a method for decontaminating or sterilizing "in situ" a vacuum sealed container and device for implementing such method for sterilizing or decontaminating microorganisms or dangerous products.

SUMMARY OF THE INVENTION

The present invention provides systems and sub-systems, and parts thereof for containing the mail at the earliest opportunity (or somewhere down the distribution line) determining whether there is hazardous material present on or in the mail, removing the mail that has hazardous material detected, from the normal distribution/sorting system, and neutralizing the hazardous material.

The present invention includes a particulate containment system capable of being connected to a biohazard detection system for analysis of the contents within the particulate containment system. Additionally, the particulate containment system can be attached to an agitation system that disturbs particulates settled on objects within the particulate containment system. An air stream can be formed within the particulate containment system to transport the disturbed particulates to an air outlet connected to the biohazard detection system.

The particulate containment system can be a vacuum mail tub in the form of a substantially rigid container and a lid. In one preferred embodiment, the container includes a vacuum port and an air vent for sampling air in the vacuum mail tub for possible biological contamination, such as anthrax. In this embodiment, the container further includes raised standoffs along the bottom of the container and channels along the walls to facilitate airflow efficiency through the vacuum mail tub when the lid is attached and a vacuum source is applied to the vacuum port. Air samples of the sealed container air are collected for contamination analysis.

For a better understanding of the present invention, together with other and further objects thereof, reference is made to the accompanying drawings and detailed description.

BRIEF DESCRIPTION OF THE DRAWINGS

FIG. 2 is partial sectional view of the lid and container rim usable in the FIG. 1 container and other embodiments of the present invention;

FIG. 3A is a schematic cross-section view of a mesh insert usable in the FIG. 1 container and other embodiments of the particulate containment system;

FIG. 3B is a schematic cross-sectional view of a subfloor with holes; and

FIGS. 4A–4C are schematic cross-sectional views of alternative air intake and air outlet embodiments usable in the FIG. 1 container and other embodiments of the particulate containment system;

DETAILED DESCRIPTION OF THE PREFERRED EMBODIMENTS

An embodiment of the particulate containment system may include a substantially rigid container having, a bottom, and sides with generally perpendicularly aligned walls forming a chamber, a rim defining an open top, and a lid. The lid is configured to substantially form an airtight seal when engaged with the rim. There is an air inlet that may automatically open to draw air into the chamber and which prohibits air from exiting the chamber. There may be an air outlet that may automatically open to exhaust air from the chamber and prohibit air from entering into the chamber. Thereby, fresh or recirculated air is drawn into the chamber by at least one one-way inlet and potentially contaminated air is drawn out of the chamber by at least one one-way outlet to allow for sampling for possible biological or other hazardous material contamination. Other embodiments of automatic air inlets and outlets include manually operated mechanisms and plugs.

Another feature of the container may include and arrangement for raising the mail from the bottom of the container, such as by using standoffs along the bottom of the container to facilitate airflow movement through the chamber when the lid is engaged to the rim of the container and, for example, a vacuum source is applied to at least one one-way outlet. The standoffs elevate mail articles above the bottom of the container, thereby creating a space where solid particulates, including contaminates, may settle. When air passes through the space, an air stream disturbs the solid particulates causing an increase in the concentration of particulates in the air stream and, thereby increasing the probability of detection of contamination by the biohazard detection system. Alternatives to the standoffs includes a mesh screen insert having legs made of suitable material such as wire or plastic or a subfloor with openings located above the bottom.

A further feature which may be used in the particulate containment system includes channels along the walls of the container to facilitate airflow movement through the chamber similar to the raised standoffs mentioned above in order to permit flow of air and particulates.

Figure 1:
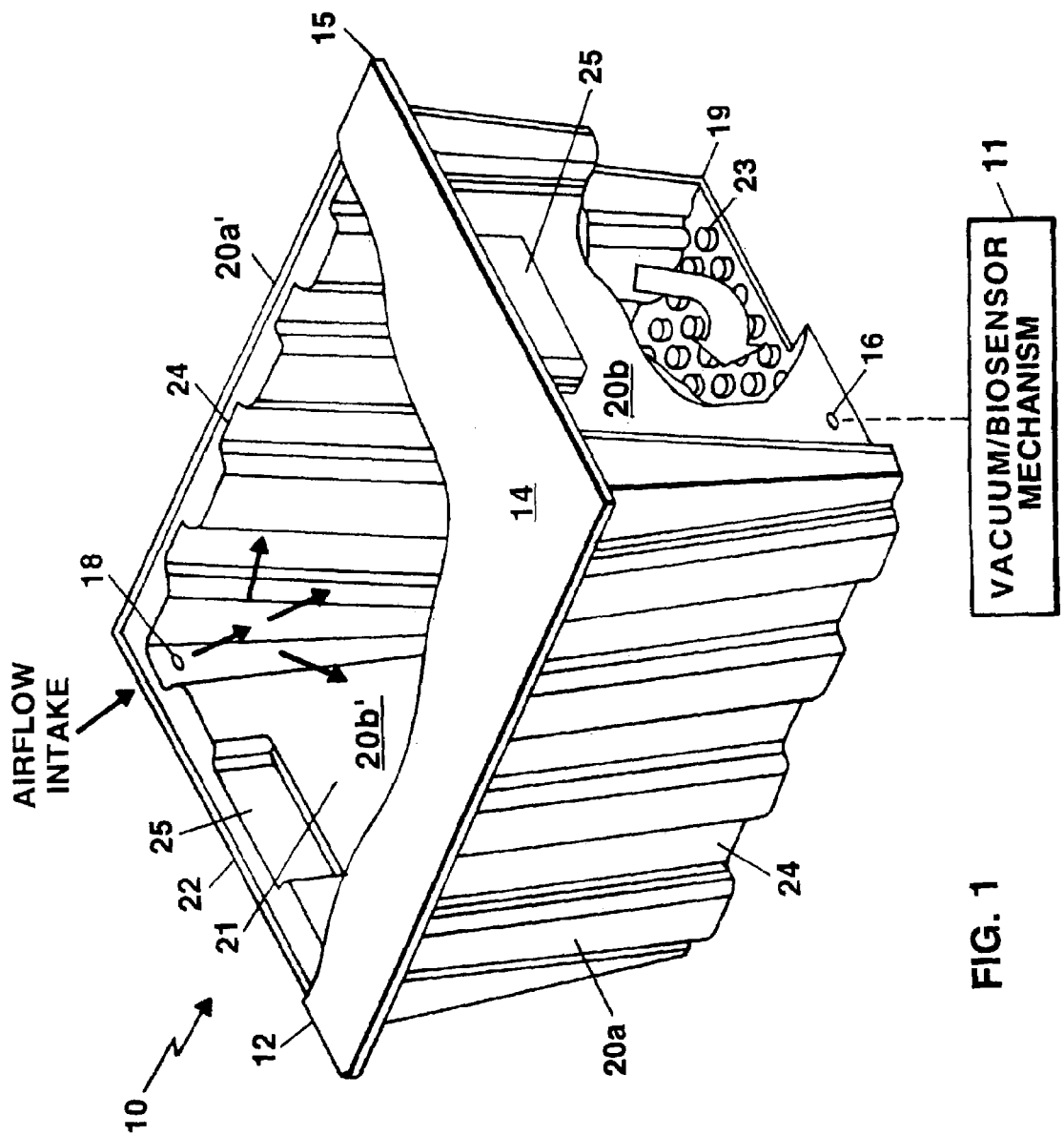
FIG. 1 is an isometric view of a particulate containment system illustrating airflow intake and circulation, and a schematic representation of such system cooperating with a vacuum/biosensor mechanism.
Figure 5:
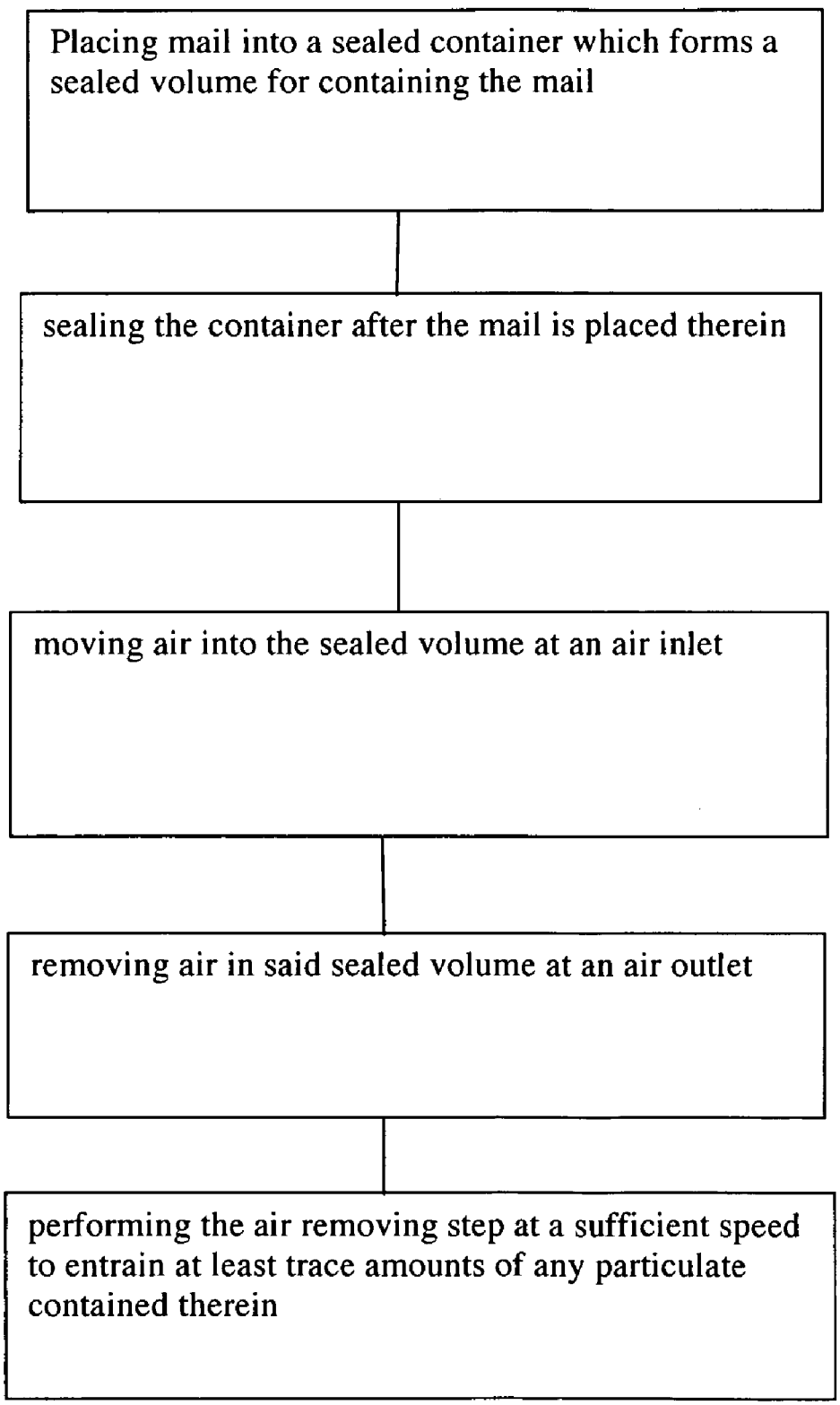
FIG. 5 is a flow chart showing the steps in the method of the present invention.

FIG. 1 shows a particulate containment system or mail tub 10 of the present invention which includes a substantially rigid container 12 and a lid 14. An air outlet or port 16 and an air intake or vent 18 are provided in container 12 for sampling air in the particulate containment system 10 for prohibited and possibly hazardous material including biological contamination, such as anthrax, and explosives.

An embodiment of the container 12, when it is a mail tub, includes a bottom wall 19, sidewalls 20a, 20a', end walls 20b, 20b', a lip 22 forming an open end 21, and molded standoffs 23 along the bottom wall 19. The container 12 may be a unitary molded structure made of any substantially rigid material, examples of which include plastic, rubber, and metal. Vertical channels 24 add strength to the container 12 and assure an unobstructed path for any particulates to travel to the air outlet 16 when a vacuum or the like is applied to air outlet 16 or a blower or the like is applied to air intake 18. Additionally, the two opposing end walls 20b, 20b' include handhold indentations 25 near the open end 21 for handlers to lift the container 12. The interior and exterior of the container 12 are configured to nest one container within another container for storage. For this purpose, the four walls may be constructed to narrow slightly from the top toward the bottom.

In the particulate container 12, a lid 14 is provided which is suitably sized and contoured to tightly fit about the lip 22 of container 12, as illustrated in FIG. 2. The lid 14 is preferably a unitary molded, generally rectangle structure made of any substantially rigid material, examples of which include plastic and rubber, which is of a sufficient width and length to extend longitudinally outwardly over the lip 22 of container 12. This allows lid 14 to form a substantially airtight seal with container 12. The edge 15 of the lid 14 is, for example, a C shape configuration forming a substantially airtight seal with the lip 22 of the container 12 and is independent of pressure.

The molded standoffs 23 (FIG. 1) prevent mail articles from resting directly on the bottom wall 19 of the container 12 and assures an unobstructed path for any particulates to travel to the air outlet 16 when a vacuum or like is applied. Additionally, the molded standoffs 23 add strength to the container 12. An alternative to molded standoffs 23 or protrusions is a mesh insert 26 having legs 33 that raise the mesh structure 35 above the bottom wall 19, as illustrated in FIG. 3A. The mesh insert 26 can be made of any suitable material, such as wire or plastic, that has sufficient strength and durability. A second alternative to molded standoffs 23 is a subfloor 27 with perforations or holes 31, illustrated in FIG. 3B. The mesh insert 26 and subfloor 27 each provides a settling area 29 for loose particles from the objects to collect for the detection process. In either construction the vertical channels 24 extend down below the mesh insert 26 or subfloor 27.

The container 12 (FIG. 1) preferably includes air intake 18 and air outlet 16 that can be arranged to be automatically opened when coupled to the biohazard detection system 11 with a negative or positive pressure device, such as a vacuum or blower or fan. The biohazard detection system can be a closed-loop system or open-loop system. The air intake 18 and air outlet 16 may be self-sealing when not attached to, for example, the biohazard detection system 11. The attachment of the biohazard detection system 11 will automatically open the air intake 18 and air outlet 16 to allow air samples to be drawn from the container 12. The air intake 18 and air outlet 16 may be similar to air chucks on a compressed air system.

The air vent 18 can be located anywhere on container 12, but is preferred on an end wall 20b' near the top open end 21. Similarly, the vacuum port 16 can be located anywhere on container 12, but is preferred on the opposing end wall 20b of the air vent 18 and near the bottom wall 19 of the container 12. The preferred locations are advantageous because air is drawn from the top of the container 12 where high concentration airborne contaminants are likely. Additionally, contaminants that settle on the bottom 19 will also by drawn from the container 12 as air travels to the vacuum port positioned the bottom wall 19.

In another embodiment, the air intake 18 and the air outlet 16 operate based on pressure differential. One-way valves may be installed within the air outlet 16 and air intake 18 for automatic closure to seal the interior of the particulate containment system 10 when vacuum is not applied, thereby assuring contaminants do not migrate into the surrounding environment. Another manner of accomplishing this is to use a HEPA filter which air is drawn through before exiting the container so that no contaminants can exit the container. For illustration purposes, examples of the above-mentioned valves are provided below.

EXAMPLE 1

Air can be forced into the container 12 by an air supply line connected to the air intake 18. In this case, the pressure within the container 12 is more than the pressure on the outside of the container 12 or on the high-pressure side of the air intake 18. Therefore, the air intake 18 opens when the pressure applied by the air supply reaches a pre-determined pressure differential level between the container internal pressure and the pressure outside the container. Once the air intake 18 opens, the pressure within the container 12 begins to rise. The air outlet 16 opens when the container pressure reaches a level greater than a predetermined level. The container air can now freely flow to the bio-detection system for analysis.

EXAMPLE 2

The air can be drawn out of the container 12 by a vacuum line connected to the air outlet 16. In this case, the pressure within the container 12 is less than the pressure on the outside of the container 12 or on the low-pressure side of the air outlet 16. Therefore, the air outlet 16 will open when the pressure applied by the vacuum decreases to a pre-determined level. Once the air outlet 16 opens, the pressure within the container 12 begins to drop and becomes lower than the pressure on the outside of the container or on the high-pressure side of the air intake 18. Therefore, the air intake 18 will open when the container pressure reaches a predetermined level. The container air can now freely flow to the bio-detection system for analysis.

In a further embodiment of the particulate containment system 10, the air intake 18 and air outlet 16 are simple port holes that are plugged with stoppers (not shown) sized to tightly fit within the port holes. Since the closure of the holes allows for the possibility of air leaking or migrating out of the container 12 while the stoppers are being installed, the operator should allow sufficient time to elapse after air sampling before disconnecting, for example the bio-detection system, from the holes, thereby maintaining the integrity of the air quality of the surrounding environment. The time delay will allow the particulates concentrated in the disturbed air to settle and the container pressure to stabilize to approximately ambient pressure. Once the air currents have sufficiently stopped within the container 12, then the bio-detection system can be disconnected and stoppers inserted in the port holes. Now the container 12 can be transported safely to the next processing station.

In additional embodiments of the particulate containment system 10, air intake 18 and air outlet 16 are a combination of three embodiments described above. For example, an automatic opening device in combination with a pressure sensitive opening device or an automatic opening device in combination with a stopper device or a pressure sensitive opening device with a stopper device. The combinations are interchangeable with the air intake 18 and the air outlet 16.

The air intake 18 can be located anywhere on container 12, but is preferred on an end wall 20b' near the top open end 21, as illustrated in FIG. 1. Similarly, the air outlet 16 can be located anywhere on container 12, but is preferred on the opposing end wall 20b of the air intake 18 and near the bottom wall 19 of the container 12, as illustrated in FIG. 1. The preferred locations are advantageous because air is drawn from the top of the container 12 where high concentration airborne contaminants are likely. Additionally, particulates that settle on the bottom 19 will also by drawn from the container 12 as air travels to the air outlet positioned the bottom wall 19.

Alternative embodiments of the particulate containment system 10 can position air intake 18 and air outlet 16 along substantially the same horizontal plane in a sidewall of a container. There are many possible embodiments. One such embodiment for illustrations purposes is along a lower horizontal plane of the container near the bottom, as illustrated FIG. 4A. In this case, the largest concentration of particulates is along the bottom and blowing or drawing air through this portion of the container may result in the maximum probability of detecting a contaminant. A second location is near the top of the container to analyze a plume of highly concentrated particulates, as illustrated FIG. 4B. A third location is along a lower horizontal plane but in the same wall, as illustrated in FIG. 4C. The optimal location for the air intake 18 and the outlet 16 is determined by the system used to sample the air from within the container 12.

When a vacuum pump is used, air may pass from the outside environment into the vacuum mail tub 10 through air vent 18 into the vacuum mail tub 10. The air exits through the vacuum port 16 when a commercially available vacuum with a biological agent sensor attachment (not shown) is attached to vacuum port 16. The air samples from the vacuum mail tub 10 are analyzed to detect a biological agent or other contaminant. If such a contaminant is detected, the vacuum port 16 and the air vent 18 can be plugged with self-sealing plugs (not shown) to seal the contamination in the vacuum mail tub and transported to a decontamination center for further processing. If desired HEPA filters may be used for this purpose.

Although the invention has been described with respect to various embodiments, it should be realized this invention is also capable of a wide variety of further and other embodiments within the spirit and scope of the present invention.

The invention claimed is:

1. A mail tub, comprising:
   a. a substantially rigid container having an open wall, means for supporting articles of mail above the bottom of the container, and channels along the walls to facilitate airflow efficiency through the container;
   b. a removable lid for sealing the open wall thereby to render the container sealed from the ambient atmosphere; and
   c. a first and a second air conducting port in said container for introducing air into the container and removing air from the container;
   said container being airtight and said lid sealing the open wall to be airtight.

2. A tub as defined in claim 1 further comprising sealing devices for airtight sealing the air ports when air is not being introduced into or removed from the container.

3. A tub as defined in claim 2 wherein said sealing devices are one-way valves or stoppers or pressure sensitive opening and closing devices or self-sealing devices.

4. A system for sampling air in sealed containers for holding articles of mail, comprising:
   a. a substantially rigid container having an open wall, means for supporting articles of mail above the bottom of the container, and channels along the walls to facilitate airflow efficiency through the container and including an air inlet port and an air outlet port for introducing air into the container and removing air from the container;

b. a removable lid for sealing the open wall thereby to render the container sealed from the ambient atmosphere; and c. an air moving assembly for connection with the air inlet port of the container, and with the air outlet port of the container for removing at least some of the air in the container for sampling and contamination analysis.

5. A system as defined in claim 4 further comprising d. means for sensing contaminants in the air removed from the container.

6. A tub as defined in claim 4 wherein the channels are open sided.

7. A system defined in claim 4 wherein said air moving assembly moves the air sufficiently to entrain particulates within the tub, and further comprising a sensor attached to the air assembly to sense whether particulates are of hazardous material.

8. A method for sampling air in a sealed volume, comprising the steps of:
   a. placing mail into a sealed container which forms a sealed volume for containing the mail, the volume having at least portions thereof along the sides and bottom which prevent the mail from contacting the sides or the bottom to permit air flow along the sides and the collection of particulate on the bottom;
   b. sealing the container after the mail is placed therein using a removable lid on the container;
   c. moving air into said sealed volume at an air inlet;
   d. removing air in said sealed volume at an air outlet
   e. performing step c. at a sufficient speed to entrain at least trace amounts of any particulate contained therein.

9. A method as defined in claim 8, further comprising the step of:
   f. sensing the air leaving the volume for hazardous materials.

10. A mail tub, comprising:
    a. a substantially rigid container having an open wall, means for supporting articles of mail above the bottom of the container, and channels along the walls to facilitate airflow efficiency through the container;
    b. a removable lid for sealing the open wall thereby to render the container sealed from the ambient atmosphere; and
    c. a first and a second air conducting port in said container for introducing air into the container and removing air from the container;
said channels being arranged to allow air flow along the walls and under the articles of mail supported above the bottom of the container.

11. A mail tub, comprising:
    a. a substantially rigid container having an open wall, means for supporting articles of mail above the bottom of the container, and channels along the walls to facilitate airflow efficiency through the container;
    b. a removable lid for sealing the open wall thereby to render the container sealed from the ambient atmosphere; and
    c. a first and a second air conducting port in said container for introducing air into the container and removing air from the container; said
means for supporting the articles of mail above the bottom of the container being arranged to allow air flow from the bottom of the container through mail located thereon.

12. A mail tub, comprising:
    a. a substantially rigid container having an open wall, means for supporting articles of mail above the bottom of the container, and channels along the walls to facilitate airflow efficiency through the container;
    b. a removable lid for sealing the open wall thereby to render the container sealed from the ambient atmosphere; and
    c. a first and a second air conducting port in said container for introducing air into the container and removing air from the container;
said supporting means being a foraminous wall and the wall being stationary.

13. A mail tub, comprising:
    a. a substantially rigid container having an open wall, means for supporting articles of mail above the bottom of the container, and channels along the walls to facilitate airflow efficiency through the container;
    b. a removable lid for sealing the open wall thereby to render the container sealed from the ambient atmosphere; and
    c. a first and a second air conducting port in said container for introducing air into the container and removing air from the container;
said supporting means is a screen and the screen is stationary.

14. A tub as defined in claim 6 wherein the channels are in the side walls.

15. A tub as defined in claim 6 wherein the channels are substantially vertical.

16. A tub as defined in claim 6 wherein the channels are formed into the side walls.

17. A system as defined in claim 7 wherein the means for supporting articles of mail above the bottom of the container provide contiguous open space throughout the bottom of the tub.

18. A system as defined in claim 17 wherein the channels have are open to said contiguous open space.

19. A system as defined in claim 18 wherein the channels and the contiguous open space are connected to have air flow throughout the tub to entrain hazardous particulate located within said container which are sensed by the sensor.

* * * * *

UNITED STATES PATENT AND TRADEMARK OFFICE
CERTIFICATE OF CORRECTION

PATENT NO.        : 7,201,037 B2                                    Page 1 of 1
APPLICATION NO. : 10/314631
DATED             : April 10, 2007
INVENTOR(S)       : Robert J. Felice et al.

It is certified that error appears in the above-identified patent and that said Letters Patent is hereby corrected as shown below:

On The Title Page, Item -56- References Cited, and further under U.S. PATENT DOCUMENTS, please add the following:

-- 4,685,274     8/1987  Garwood ..................53/433
   6,074,608     6/2000  Matz .........................422/83 --

On The Title Page Item (-56-) References Cited, and further under FOREIGN PATENT DOCUMENTS, please add the following:

-- FR   1108036    A      1/1956
   BE   1005515    A3     8/1993
   DE   19753185   A1     6/1999
   EP   1092649    A1     4/2001--

On The Title Page, Item -56- References Cited, and further under OTHER PUBLICATIONS, please add the following:

-- International Search Report , 07/23/03, PCT/US02/39280 (12078-159PCT).

WO 03/055772, Published PCT International Application, Publication Date 07/10/03, PCT/US02/39280 (12078-159PCT). --

Signed and Sealed this

Twenty-sixth Day of June, 2007

JON W. DUDAS
*Director of the United States Patent and Trademark Office*